(12) United States Patent
Nilsson

(10) Patent No.: US 11,324,274 B2
(45) Date of Patent: May 10, 2022

(54) WELDING HELMET

(71) Applicant: 3M INNOVATIVE PROPERTIES COMPANY, St. Paul, MN (US)

(72) Inventor: Mathilda Nilsson, Borlänge (SE)

(73) Assignee: 3M Innovative Properties Company, St. Paul, MN (US)

( * ) Notice: Subject to any disclaimer, the term of this patent is extended or adjusted under 35 U.S.C. 154(b) by 131 days.

(21) Appl. No.: 16/644,063

(22) PCT Filed: Sep. 19, 2018

(86) PCT No.: PCT/IB2018/057225
§ 371 (c)(1),
(2) Date: Mar. 3, 2020

(87) PCT Pub. No.: WO2019/058282
PCT Pub. Date: Mar. 28, 2019

(65) Prior Publication Data
US 2020/0405000 A1    Dec. 31, 2020

(30) Foreign Application Priority Data
Sep. 22, 2017   (GB) .................................... 1715417

(51) Int. Cl.
*A61F 9/06* (2006.01)
*A42B 3/12* (2006.01)
*A42B 3/22* (2006.01)

(52) U.S. Cl.
CPC .............. *A42B 3/127* (2013.01); *A42B 3/225* (2013.01); *A61F 9/06* (2013.01)

(58) Field of Classification Search
CPC ............ A42B 3/127; A42B 3/225; A61F 9/06
See application file for complete search history.

(56) References Cited

U.S. PATENT DOCUMENTS

| | | | |
|---|---|---|---|
| 1,602,727 A | 10/1926 | Turner | |
| 2,889,606 A * | 6/1959 | Bowers, Sr. | .............. A61F 9/06 403/66 |
| 3,026,525 A | 3/1962 | Gyorfy | |
| 3,600,714 A | 8/1971 | Cade | |
| 4,117,554 A | 10/1978 | Palumbo | |
| 2004/0078859 A1 | 4/2004 | Inget | |

(Continued)

FOREIGN PATENT DOCUMENTS

| | | |
|---|---|---|
| KR | 1020110078467 | 7/2011 |
| KR | 1020130025534 | 3/2013 |

OTHER PUBLICATIONS

International Search Report for PCT International Application No. PCT/IB2018/057225, dated Dec. 19, 2018, 6 pages.

*Primary Examiner* — Tajash D Patel
(74) *Attorney, Agent, or Firm* — Gregg H. Rosenblatt

(57) ABSTRACT

A welding helmet (1) comprising a head suspension unit and a protective shield (2), the protective shield being pivotally mounted on the head suspension unit between a lowered position in which the protective shield covers a wearer's face, and an upraised position in which the protective shield uncovers the wearer's face, the head suspension unit comprising a head cover (100) for covering the wearer's head, wherein the head suspension unit includes a removable configurable scrape guard (110) to protect the wearer's head from impact.

10 Claims, 5 Drawing Sheets

(56) References Cited

U.S. PATENT DOCUMENTS

| | | | |
|---|---|---|---|
| 2014/0298557 A1* | 10/2014 | Townsend, Jr. | A41D 31/08 |
| | | | 2/8.2 |
| 2016/0074230 A1* | 3/2016 | Sernfalt | A42B 3/225 |
| | | | 2/8.3 |
| 2016/0361201 A1 | 12/2016 | Sommers | |
| 2021/0015672 A1* | 1/2021 | Huh | B23K 9/322 |

* cited by examiner

WELDING HELMET

FIELD OF THE INVENTION

The invention relates to a welding helmet and in particular to a welding helmet that has a scrape guard that is removably attachable to a head cover of the welding helmet.

BACKGROUND ART

Welding Helmets are typically used in the mechanical and industrial art to protect welders from harmful irradiation emitted from the welding arc and from splashes, sparks and particles that may be ejected from a welding area. Welding helmets typically can be suspended on the head of a wearer, so that the wearer has both hands available for welding and handling of workpieces.

Some welding helmets are furnished with an automatic darkening filter. An automatic darkening filter commonly has a switchable filter that automatically changes from a light-state to a dark-state in response to incident light generated by the welding arc. Thus, upon ignition of the welding arc the switchable filter automatically changes to the dark-state and protects the welder's eyes and face from the irradiation emitted from welding arc. Once the welding is interrupted or ended the switchable filter automatically changes to the light-state so that the user can see through the filter at normal light conditions.

Accordingly, there are welding helmets that stay in position on a wearer's head independent from the actual welding actions, for example during locating of the electrode toward the workpiece to be welded or during handling.

Often the wearer is working in a confined space. The wearer may be in close proximity to the workpiece or even inside the workpiece in the case of pipe welding for example. As a result, the wearer's head may be inside workpieces or in close proximity to the workpiece or other hard objects such as overhead beams or pipes. It is not uncommon therefore for the wearer to bump or scrape their head on such hard or sharp objects.

Since it is not possible to wear separate head protection in conjunction with such welding helmets as described above, it is known to provide the wearer with a bump cap to offer a degree of protection against injury.

For example, US 2016/0361201 A1 discloses a system for attaching a bump cap to welding headgear.

However, such bump caps as are known and exemplified in US 2016/0361201 A1 are often heavy, large, and/or inflexible causing discomfort to the wearer.

An object of the current invention is therefore to provide head protection for a welding mask that provides improved comfort for the wearer whilst continuing to fulfill the safety requirements in the field of welding.

SUMMARY OF THE INVENTION

According to a first aspect of the invention there is provided a welding helmet comprising a head suspension unit and a protective shield, the protective shield being pivotally mounted on the head suspension unit between a lowered position in which the protective shield covers a wearer's face, and an upraised position in which the protective shield uncovers the wearer's face, the head suspension unit comprising a head cover for covering the wearer's head, wherein the head suspension unit includes a removable scrape guard to protect the wearer's head from impact.

According to a second aspect of the invention there is provided a scrape guard for a welding helmet, the welding helmet comprising a head suspension unit and a protective shield, the protective shield being pivotally mounted on the head suspension unit between a lowered position in which the protective shield covers a wearer's face, and an upraised position in which the protective shield uncovers the wearer's face, the head suspension unit comprising a head cover for covering the wearer's head, wherein the scrape guard is selectively positionable within the head suspension unit and is configurable to the shape of the head of the wearer so as to protect the wearer's head from impact.

These aspects of the invention are advantageous in that they provide for a welding helmet that allows for the extent of head protection afforded to the user to be varied dependent on the particular workpiece or work environment. For example, when the wearer wishes to have head protection but is not exposed to hard or sharp objects in the vicinity of the workpiece they may use the head cover but remove the scrape guard. Equally, if the wearer is working in a confined space where there is a risk of the head impacting a sharp and/or hard object (such as a steel beam for example) they may reinstall the scrape guard easily and quickly. The wearer is therefore able to maximize their comfort whilst at all times ensuring they work with the level of protection appropriate for the work environment.

Preferably, the head cover is a soft head cover.

Advantageously, this feature of the invention maximizes the comfort afforded by the head cover when the risk of head impact is minimal.

Preferably, the scrape guard is positioned inside the head cover.

Advantageously, this feature of the invention ensures that the scrape guard forms a close fit to the wearer's head thereby maximizing comfort and the extent of safety protection offered by the guard. It also enables easy fitting and removal of the scrape guard to and from the head cover.

Preferably, the scrape guard is removably attached to soft head shield.

Preferably, the scrape guard is removably attached to soft head cover by hook and loop connection.

Preferably, the scrape guard has a soft lining on a head-facing surface.

Advantageously, this feature of the invention maximizes the comfort and the extent of safety protection offered by the guard.

Preferably, the scrape guard is configurable to match a shape of the wearer's head.

This feature of the invention delivers the significant advantage that the scrape guard can be configured to the particular shape of the head of the user. The soft head cover will naturally conform to the shape of the wearer's head. However, known bump caps are heavy and of a fixed shape and cannot be so configured. This feature increases the comfort experienced by the user wearing the scrape guard and also ensures the safety of the user by minimizing the risk of the scrape guard moving out of position as a result of poor fitment.

Preferably, the scrape guard has a circular profile and a series of radially extending protrusions.

Preferably, the radially extending protrusions bend downwardly in use so as to form a substantially dome-shaped cap.

Preferably, the scrape guard is configurable by altering the extent of the downward bend of the radially extending protrusions so as to alter the shape of the cap.

BRIEF DESCRIPTION OF THE FIGURES

The invention will now be described, by way of example only, and with reference to the following drawings, in which.

DETAILED DESCRIPTION OF THE INVENTION

Figure 1:
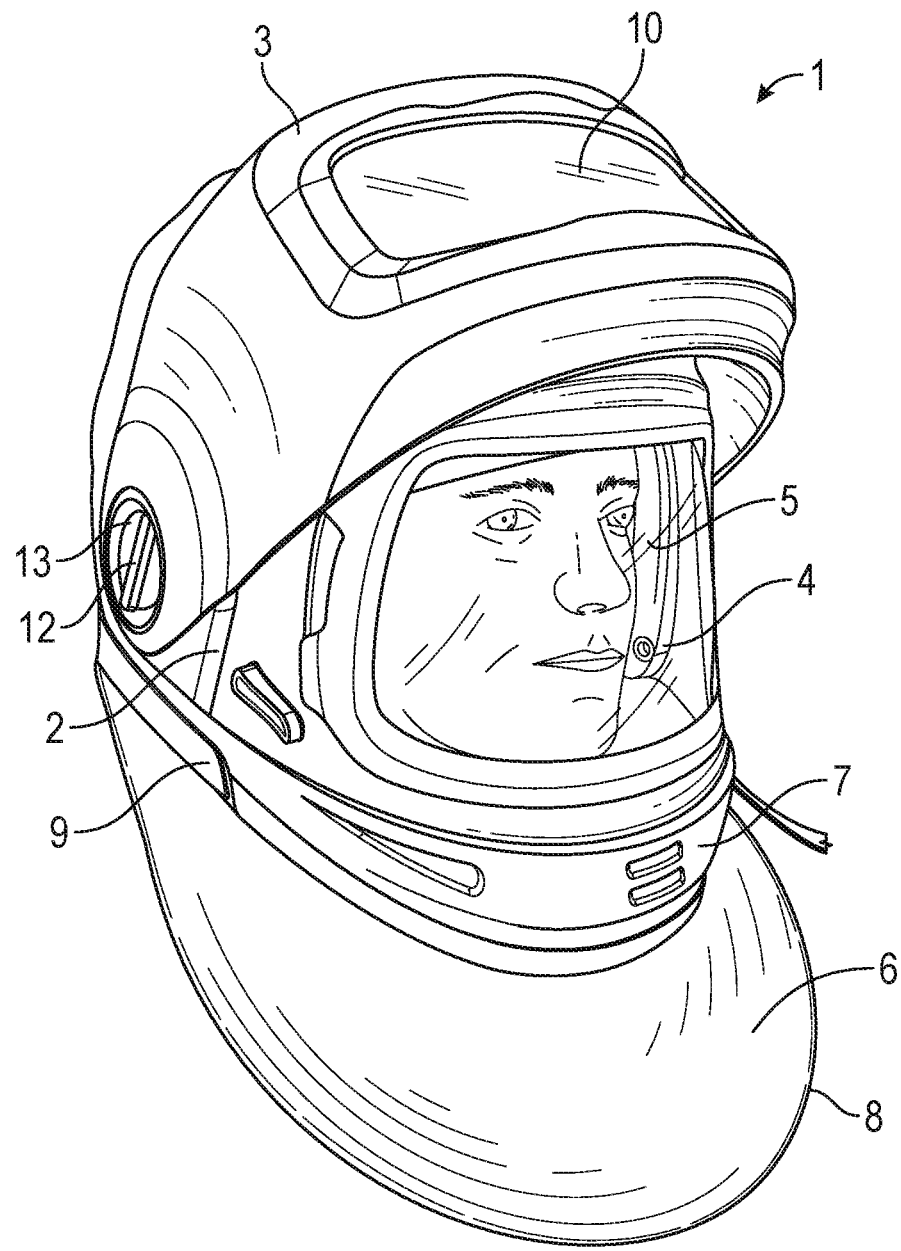
FIG. 1 is a perspective view of a welding helmet according to a first aspect of the invention.

FIG. 1 shows a welding helmet 1 which has a protective shield 2 and a movable visor 3. The protective shield 2 is sized and shaped to cover a wearer's face and the upper part and lateral sides of the wearer's head. The movable visor 3 is arranged on an outside of the protective shield 2. Further the movable visor 3 is pivotably suspended at the welding helmet 1 relative to the see-through window. The movable visor 3 is thus pivotable so that it can be positioned between a first position (not shown in this Figure) in which the movable visor covers the see-through window and a second position (as shown in this Figure) in which the movable visor 3 uncovers the see-through window. The movable visor 3 is suspended at a pivot mechanism 13 which has a knob 12 for adjusting a friction between the movable visor 3 and the protective shield 2. Accordingly, the knob 12 allows for retaining the movable visor 3 and the protective shield 2 relative to each other so that the movable visor 3 is prevented from moving by its own weight (for example from the first toward the second position).

The movable visor 3 comprises an automatic darkening filter 10. The automatic darkening filter 10 allows a welder to safely observe the welding arc during welding. In the example the automatic darkening filter 10 is based on two liquid crystal cells. The liquid crystal cells are electrically switchable between a light-state and a dark-state. When switched in the dark-state, the automatic darkening filter 10 blocks a significant amount of light from being transmitted therethrough. This enables a user to observe a welding arc by seeing through the automatic darkening filter 10 without risking exposure to harmful light radiation from the welding arc. In the light-state the automatic darkening filter 10 permits a significant amount of light to be transmitted therethrough. Thus, the automatic darkening filter 10 in the light-state allows the user to see under ambient light conditions (in the absence of the welding arc). The two (or more) liquid crystal cells are arranged optically in sequence. This provides for multiplying the darkening effect (in particular in the dark-state) and thus a sufficient eye protection from light radiation.

Further, the welding helmet 1 comprises at least one light sensor (not shown) and electronic circuitry that causes the liquid crystal cells to switch dependent on light recognized by the light sensor(s). In particular, the light sensor may provide a signal to the electronic circuitry depending on the light sensed by the light sensor. The signal provided by the light sensor can typically be correlated to the intensity of light sensed by the light sensor. The electronic circuitry is set up to control the switching of the automatic darkening filter to the dark-state in case the light intensity (and optionally an additional frequency or pulsation) detected by the light sensor is within a predetermined range of values or exceeds a predetermined value. Further, the electronic circuitry is set up to control the switching of the automatic darkening filter to the light-state in case the light intensity detected by the light sensor is outside the predetermined range of values or falls below a predetermined value.

The protective shield 2 of the welding helmet 1 forms a see-through window 4 that is closed by a fixed visor 5. The fixed visor 5 is formed by a clear polymeric panel, which in the example is made of polycarbonate. The fixed visor 5 is fixed at the protective shield 2 and covers, in particular seals, the see-through window 4. The fixed visor 5 may for example be used to protect a wearer of the welding helmet 1 during grinding works. Further, in the first position of the movable visor 3 the see-through window 4 (with the fixed visor 5) overlaps with the movable visor 3 so that a wearer of the welding helmet 1 can see through both, the see-through window 4 (with the fixed visor 5) and the movable visor 3.

The welding helmet further has a neck shield 6. The neck shield 6 provides for protecting a wearer's neck from harmful light as for example emitted from a welding arc, and from particles, for example splashes or particles as they may be ejected during welding and/or grinding. The neck shield 6 is attached at a lower end 7 of the protective shield 2. The attachment of the neck shield is reversible. This means that the neck shield 6 is removable from the protective shield 2. In particular the neck shield 6 is removable from the protective shield 2 without damaging or breaking any of the neck shield 6 or the protective shield 2. In the example the neck shield 6 has a bib 8 which is flexible. The bib 8 in the example is made of a fabric, in particular a fabric. The neck shield 6 further has an attachment frame 9 at which the bib 8 is fixed. The neck shield 6 of the example corresponds to the "second neck shield" as referred to in the Summary of the invention.

Figure 2:
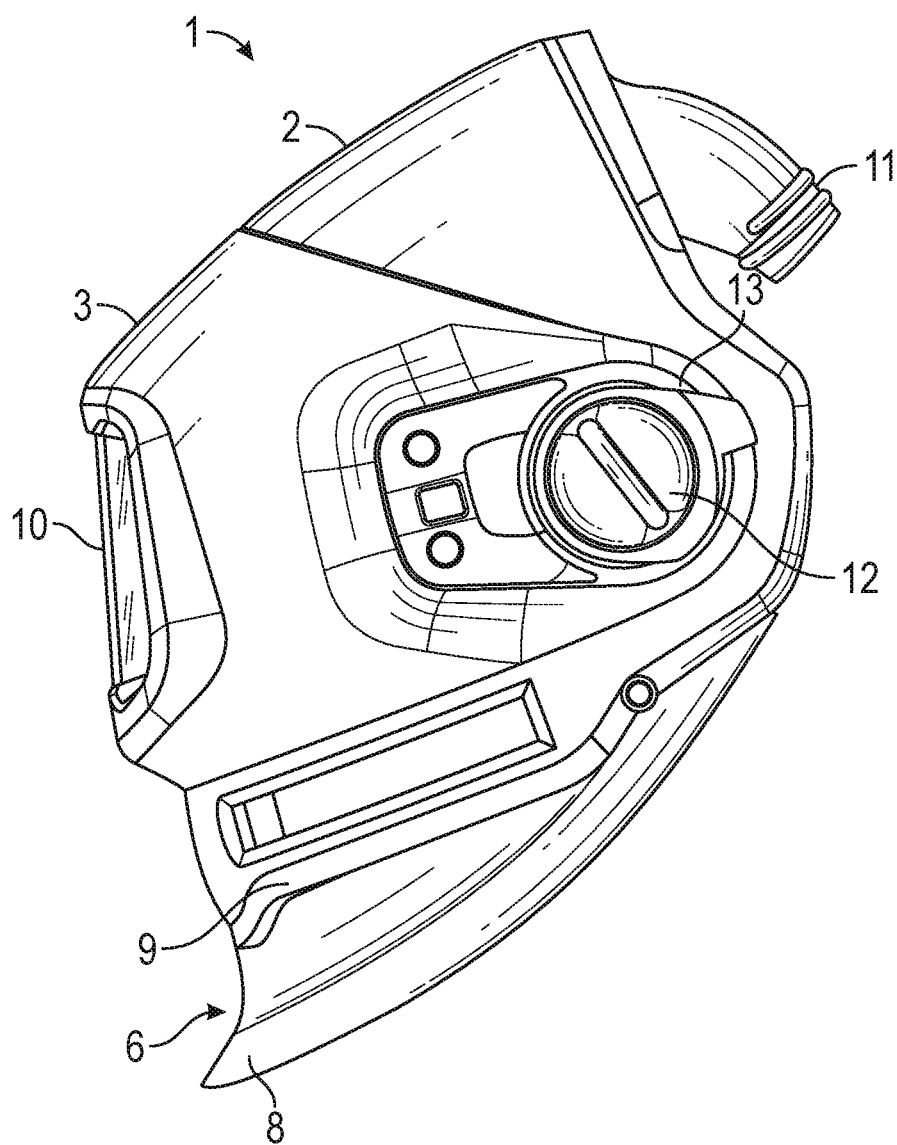
FIG. 2 is a side view of the welding helmet of FIG. 1.

FIG. 2 shows the same welding helmet 1 as shown in FIG. 1 in a side view but with a head cover 100 fitted. The welding helmet 1 has an inlet 11 for connecting the welding helmet 1 with an air supply via a hose (not shown). Such an air supply may for example by a powered air purifying unit as known in the field of powered air purifying respirators (PAPRs). Thus, a wearer of the welding helmet 1 can be supplied with fresh air forced between the protective shield 2 and the wearer's head (and face).

Figure 3:
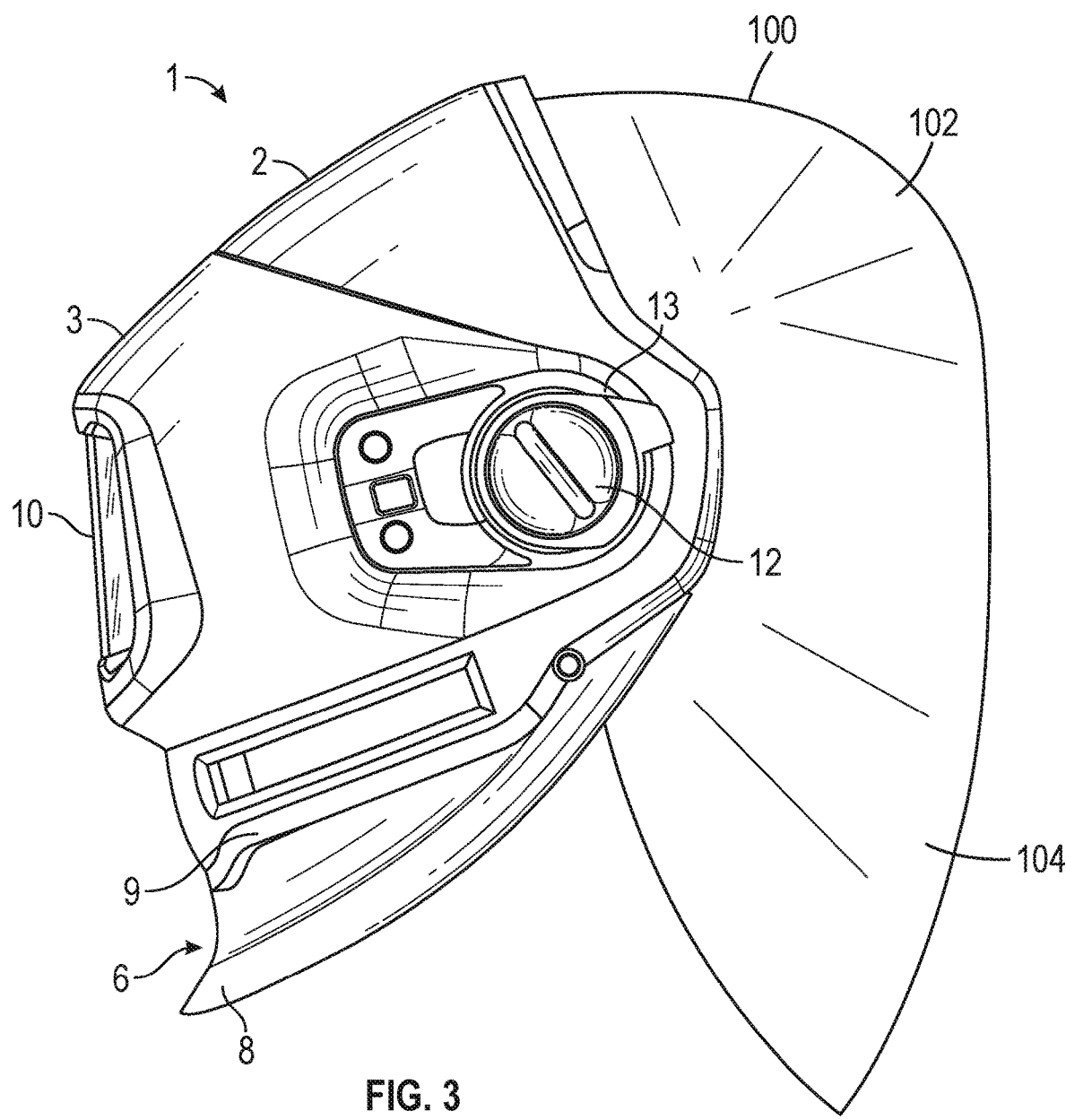
FIG. 3 is a side view of the welding helmet of FIG. 2 shown with a head cover in place.

FIG. 3 shows the same welding helmet 1 as shown in FIG. 2 in a side view but with a head cover 100 fitted. The head cover 100 covers and thereby protects the head of the user from environmental factors such as debris and heat. The cover 100 also assists in accommodating the positive pressure air supplied by through the inlet 11.

The head cover 100 has an upper head section 102 and a lower neck section 104. The upper head section 102 conforms broadly to the shape of the head. The lower neck section 104 extends downwardly and rearwardly from the neck to provide air space between the neck of the user and the head cover 100. The head cover 100 is formed from a compliant material and may have stiffening elements in the upper head section 102 and/or a lower neck section 104 in order to provide additional rigidity.

Figure 4:
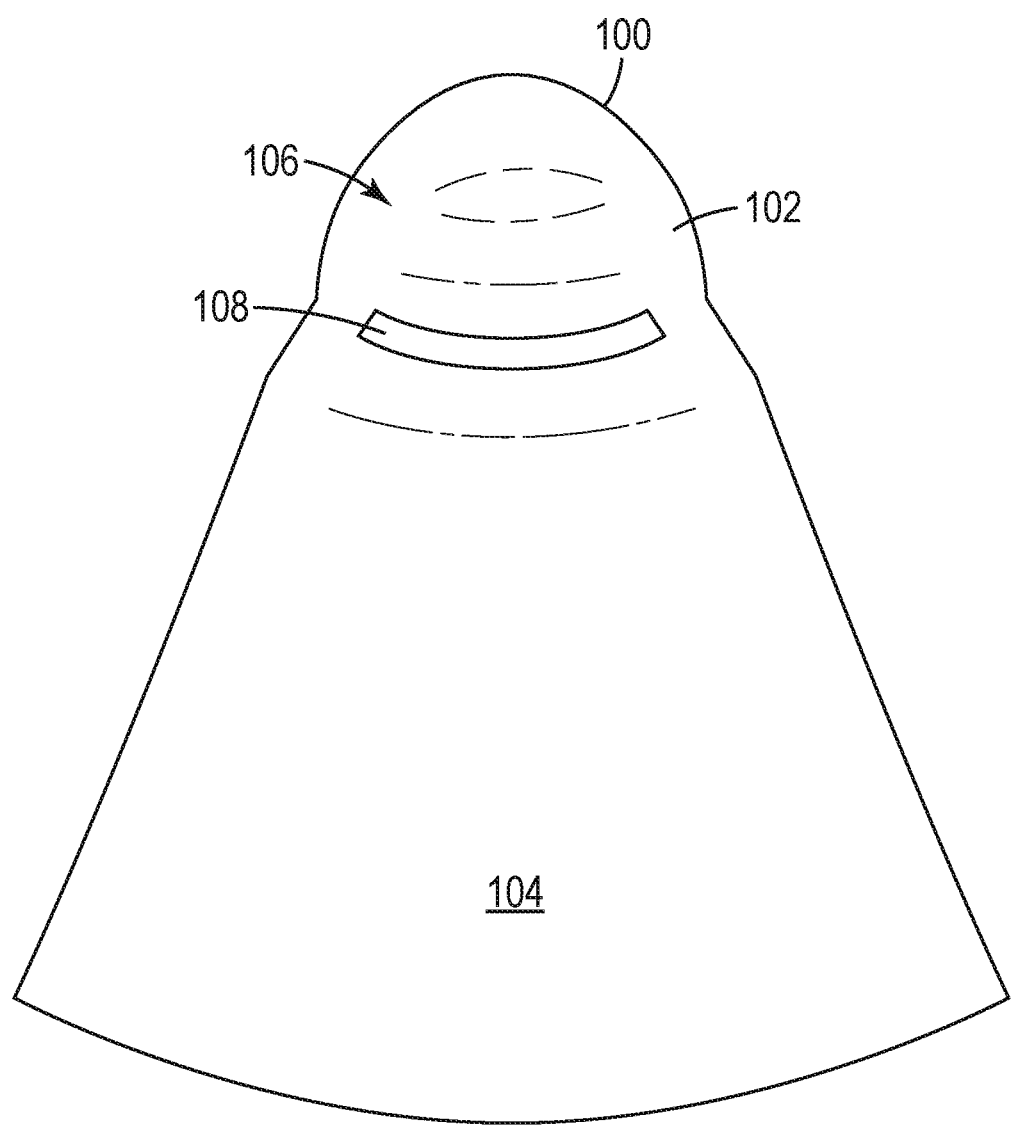
FIG. 4 is a perspective internal view of part of the head cover shown in FIG. 3 without the scrape guard of a second aspect of present invention fitted.

Turning now to FIG. 4, an inner surface 106 of the upper head section 102 of the head cover 100 is shown. This inner surface 106 accommodates a releasable scrape guard 110 (not shown but described in further detail below with reference to FIG. 5). In order to releasably affix the scrape guard 110 thereto the inner surface 106 of the upper head section 102 has a scrape guard attachment means in the form of attachment strip 108. In this embodiment of the invention the strip 108 is one half of a hook and loop connection system, in this instance the loop section with hook section being provided on the scrape guard 110. It is conceivable within the scope of the invention that the scrape guard 110 is attached to the head cover 100 by alternative releasable fixing means such as releasable adhesive.

Figure 5:
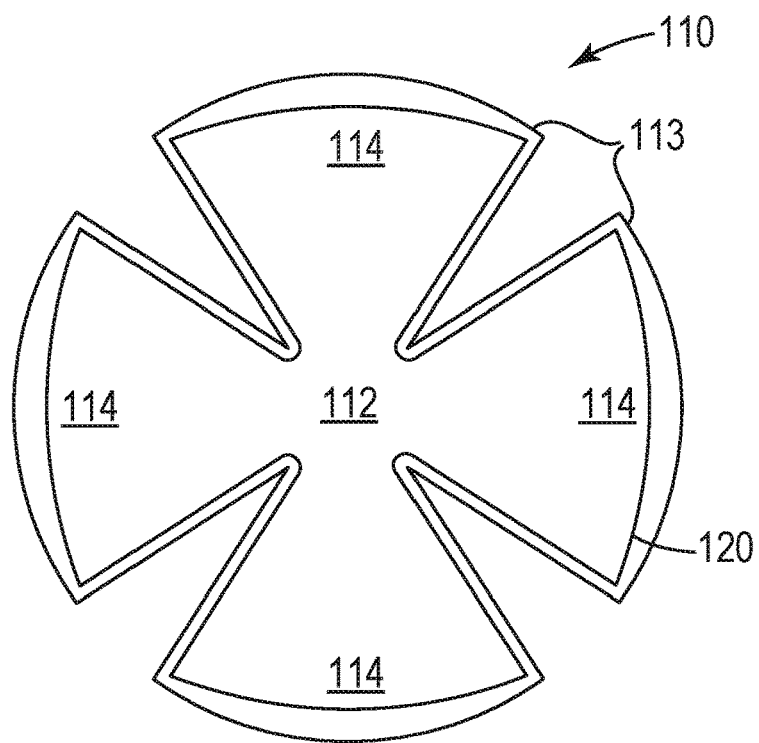
FIG. 5 is a plan view of the scrape guard of the second aspect of the present invention.

FIG. 5 shows the scrape guard 110 in further detail in its flat unused state. The guard 110 has a central section 112, a substantially circular outer profile 113 and four radially outwardly extending portions 114. It is conceivable within the scope of the invention that the scrape guard 110 could have an alternative number of protrusions without departing from the purpose of the protrusions to provide for conformability to the head of the wearer as will be described in further detail below. The guard 110 is formed from a die cut plastic that is elastically deformable to allow for conformity with the head of the wearer. The plastic is soft enough to be bent whilst being hard enough to protect the head of the user from impact against hard surfaces and sharp objects. The scrape guard 110 has a soft insert 120 which provides a soft and comfortable interface with the wearer's head.

Figure 6:
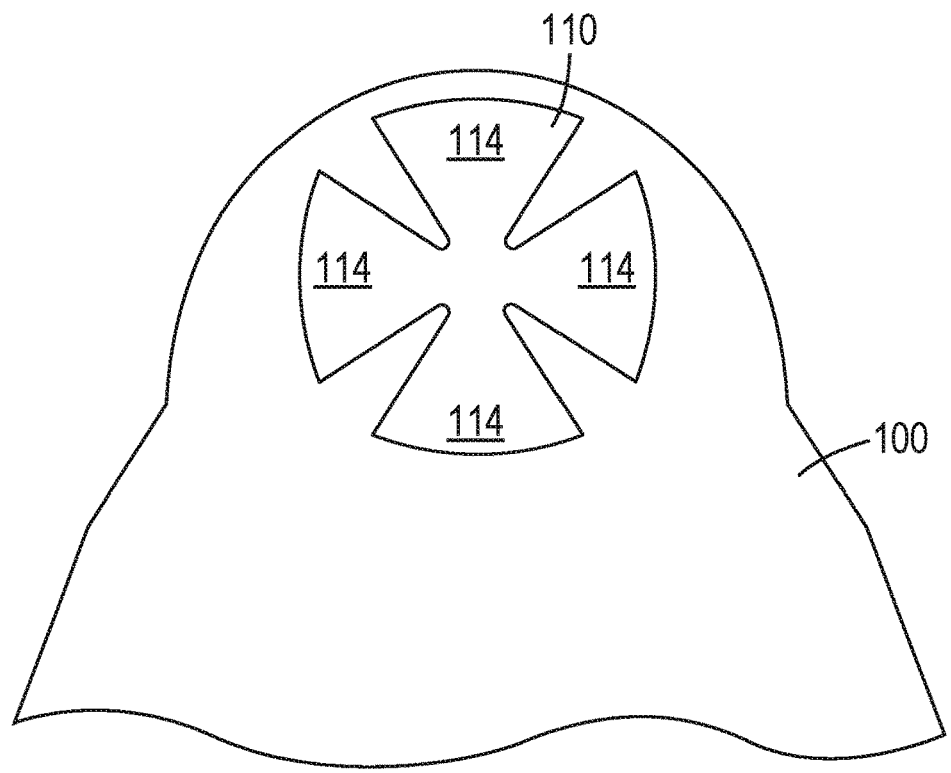
FIG. 6 is a perspective internal view of part of the head cover shown in FIG. 3 with the scrape guard of FIG. 5 fitted.

FIG. 6 shows the scrape guard 110 in use and releasably attached to the head cover 100 via the attachment strip 108. The radially outwardly extending portions 114 have bent about the central section 112 and along their length such that the gap between the portions 114 has reduced causing the guard 110 to form substantially dome-shaped cap. The specific dimensions of the dome-shaped are further configured upon the wearer donning the head cover 100.

Accordingly, the wearer may advantageously use or remove the scrape guard 110 dependent on the work environment. Furthermore, the scrape guard, when in use, is advantageously configurable to the shape of the head of the user by virtue of the conformable outwardly extending portions 114.

The invention claimed is:

1. A welding helmet comprising a head suspension unit and a protective shield, the protective shield being pivotally mounted on the head suspension unit between a lowered position in which the protective shield covers a wearer's face, and an upraised position in which the protective shield uncovers the wearer's face, the head suspension unit comprising a head cover for covering the wearer's head, wherein the head cover comprises a soft head cover, wherein the head suspension unit includes a removable scrape guard positioned inside the soft head cover to protect the wearer's head from impact.

2. The welding helmet of claim 1, wherein the scrape guard is removably attached to soft head shield.

3. The welding helmet of claim 2, wherein the scrape guard is removably attached to soft head cover by hook and loop connection.

4. The welding helmet of claim 1, wherein the scrape guard has a soft lining on a head-facing surface.

5. The welding helmet of claim 1, wherein the scrape guard has a circular profile and a series of radially extending protrusions.

6. The welding helmet of claim 5, wherein the radially extending protrusions bend downwardly in use so as to form a substantially dome-shaped cap.

7. The welding helmet of claim 6, wherein the scrape guard is configurable by altering the extent of the downward bend of the radially extending protrusions so as to alter the shape of the cap.

8. The welding helmet of claim 1, wherein the soft head cover comprises an upper head section and a lower neck section, wherein the upper head section conforms broadly to the shape of the head and the lower neck section extends downwardly and rearwardly from a neck area of a user to provide air space between the neck area of the user and the head cover.

9. The welding helmet of claim 1, wherein the scrape guard comprises a plastic material that is elastically deformable to allow for conformity with the head of the wearer.

10. The welding helmet of claim 9, wherein the plastic comprises a bendable material having a hardness sufficient to protect the head of the user from impact against hard surfaces and sharp objects.

\* \* \* \* \*